(12) United States Patent
De Pater et al.

(10) Patent No.: US 10,954,272 B2
(45) Date of Patent: Mar. 23, 2021

(54) METHOD FOR ACYLATING A CYCLIC PEPTIDE

(71) Applicant: DSM Sinochem Pharmaceuticals Netherlands B.V., Delft (NL)

(72) Inventors: Robertus Mattheus De Pater, Echt (NL); Ben De Lange, Echt (NL)

(73) Assignee: Centrient Pharmaceuticals Netherlands B.V.

( * ) Notice: Subject to any disclaimer, the term of this patent is extended or adjusted under 35 U.S.C. 154(b) by 0 days.

(21) Appl. No.: 15/535,306

(22) PCT Filed: Dec. 4, 2015

(86) PCT No.: PCT/EP2015/078651
§ 371 (c)(1),
(2) Date: Jun. 12, 2017

(87) PCT Pub. No.: WO2016/091746
PCT Pub. Date: Jun. 16, 2016

(65) Prior Publication Data
US 2017/0327540 A1    Nov. 16, 2017

(30) Foreign Application Priority Data

Dec. 11, 2014 (EP) .................................. 14197387

(51) Int. Cl.
*A61K 38/00* (2006.01)
*C07K 7/56* (2006.01)

(52) U.S. Cl.
CPC ..................................... *C07K 7/56* (2013.01)

(58) Field of Classification Search
None
See application file for complete search history.

*Primary Examiner* — Jeanette M Lieb
(74) *Attorney, Agent, or Firm* — William D. Hare, Esq.; McNeely, Hare & War, LLP

(57) ABSTRACT

The present invention relates to a process for acylating cyclic peptides bearing an amino group and to the application of said process in the preparation of anidulafungin and micafungin.

10 Claims, No Drawings

METHOD FOR ACYLATING A CYCLIC PEPTIDE

FIELD OF THE INVENTION

The present invention relates to a process for acylating cyclic peptides bearing an amino group and to the application of said process in the preparation of anidulafungin and micafungin.

BACKGROUND OF THE INVENTION

Cyclic peptides can be naturally occurring compounds but may also be obtained by total synthesis or by synthetic or genetic modification of naturally occurring or naturally produced precursors. The latter class is referred to as semi synthetic cyclic peptides. When cyclic peptides bear one or more lipid tails or acyl chains, such cyclic peptides are referred to as cyclic lipopeptides. Cyclic lipopeptides with antibiotic and/or antifungal activity include compounds such as daptomycin and amphomycin and an excellent example of cyclic lipopeptides is the class of echinocandins which are potent antifungals. Echinocandins are amphiphilic hexapeptides with an N-linked acyl lipid side chain and a molecular weight of between 1000 and 1400 Da. Examples of medicinally useful echinocandins are the cyclic hexapeptides anidulafungin (formula (A)), caspofungin, cilofungin and micafungin (formula (B)) which are useful in treating fungal

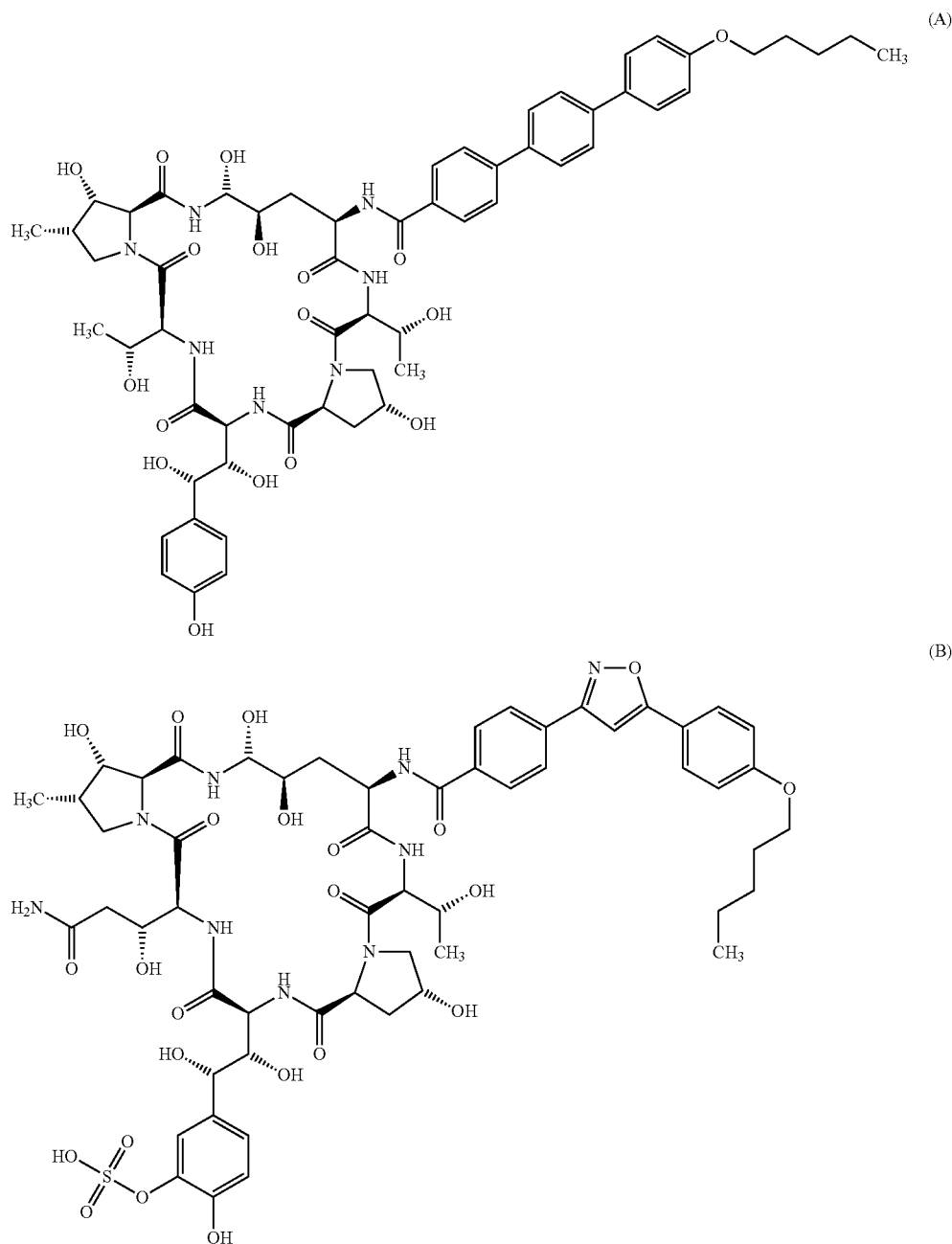

infections, especially those caused by *Aspergillus, Blastomyces, Candida, Coccidioides* and *Histoplasma*. Anidulafungin (1-[(4R,5R)-4,5-dihydroxy-N2-[[4"-(pentyloxy)[1, 1':4',1"'-terphenyl]-4-yl]carbonyl]-L-ornithine]echinocandin B), caspofungin (1-[(4R,5S)-5-[(2-aminoethyl)amino]-N2-(10,12-dimethyl-1-oxotetra-decyl)-4-hydroxy-L-ornithine]-5-[(3R)-3-hydroxy-L-ornithine]pneumocandin $B_0$) and micafungin (1-[(4R,5R)-4,5-dihydroxy-N2-[4-[5-[4-(pentyloxy)phenyl]-3-isoxazolyl]benzoyl]-L-ornithine]-4-[(4S)-4-hydroxy-4-[4-hydroxy-3-(sulfooxy)phenyl]-L-threonine] pneumocandin $A_0$) are all semi synthetic cyclic hexapeptides derivable from naturally occurring echinocandins such as for instance echinocandin B, pneumocandin $A_0$, pneumocandin $B_0$ or FR 901379. In industry, FR 901379 is the generally accepted code for 5-((1S,2S)-2-((2R,6S,9R,11R,12R,14aS, 15S,16S,20S,23S,25aS)-20-((R)-3-amino-1-hydroxy-3-oxopropyl)-2,11,12,15-tetrahydroxy-6-((R)-1-hydroxyethyl)-16-methyl-5,8,14,19,22,25-hexa-oxo-9-palmitamidotetracosahydro-1H-dipyrrolo[2,1-c:2',1'-l][1,4,7,10,13,16]hexaazacyclohenicosin-23-yl)-1,2-dihydroxyethyl)-2-hydroxyphenyl hydrogen sulfate (CAS 144371-88-0; $C_{51}H_{82}N_8O_{21}S$).

Natural cyclic lipopeptides are typically produced by micro-organisms. Daptomycin is produced by the soil bacterium *Streptomyces roseosporus*. Amphomycin is produced by *Streptomyces canus*. Natural echinocandins such as echinocandin B, echinocandin C, aculeacin Aγ, pneumocandin $B_0$ and FR 901379 are also typically produced by various micro-organisms. For example, echinocandin B is produced by the fungus *Aspergillus nidulans* and FR 901379 is produced by the fungus *Coleophoma empetri*.

The acyl chain of cyclic lipopeptides has shown to be an important determinant of antifungal activity and toxicity (Debono M. & Gordee R. S., *Annu. Rev. Microbiol.* 48, 471 (1994)). For instance the naturally occurring cyclic antifungal lipopeptide FR 901379 bearing a fatty acid acyl group attached to the N-terminus shows potent in vivo antifungal activity (Iwamoto, T., Fujie A., Nitta, K., Hashimoto, S., Okuhara, M., Kohsaka, M., *J. Antibiot.* 47, 1092 (1994). Unfortunately, just like some other naturally occurring echinocandins it also shows high hemolytic activity. Enzymatic removal of the fatty acid chain and replacement for an octyloxybenzoyl acyl chain showed that the original activity of FR 901379 was retained but that hemolytic activity was significantly reduced. Another example is micafungin, which is produced by exchanging the lipid tail of FR 901379 for a complex 3,5-diphenyl substituted isoxazole acyl group (Fujie, *Pure Appl. Chem.* 79, No. 4, pp. 603-614 (2007)). Deacylation of the natural acyl chain of cyclic lipopeptides thus allows for the introduction of alternative side chains which improve antifungal efficacy and decrease hemolytic activity.

Deacylation of cyclic lipopeptides, such as echinocandins, has been established by means of the Aculeacin A acylase from *Actinoplanes utahensis*. JP 4228072(A) discloses an enzyme that catalyzes the deacylation of the lipid acyl portion of lipid cyclic peptide metabolites such as echinocandin B and aculeacin. JP 4075585 describes that this acylase can be cultured in *Streptomyces* as host organism. After Aculeacin A acylase is collected from a culture solution it is directly used to deacylate a substrate. In the course of optimizing the enzymatic deacylation it was discovered that some acylases of *Streptomyces* species were more efficient. EP 0885957 A1 describes cyclic lipopeptide acylases from the genus *Streptomyces* which are capable of deacylating the acyl chain of a cyclic lipopeptide compound, e.g. the abovementioned echinocandin FR 901379 or analogs thereof and a method of producing a cyclic peptide compound which comprises using said acylases. Finally, deacylation of cyclic lipopeptides on industrial scale by providing a method that applies an acylase that is producible in a functional form in an industrially preferred production host such as *Pseudomonas* has been reported in WO 2014/044803.

(C)

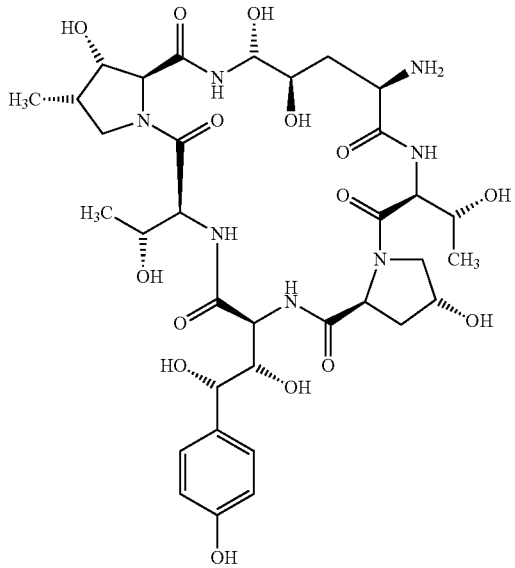

(D)

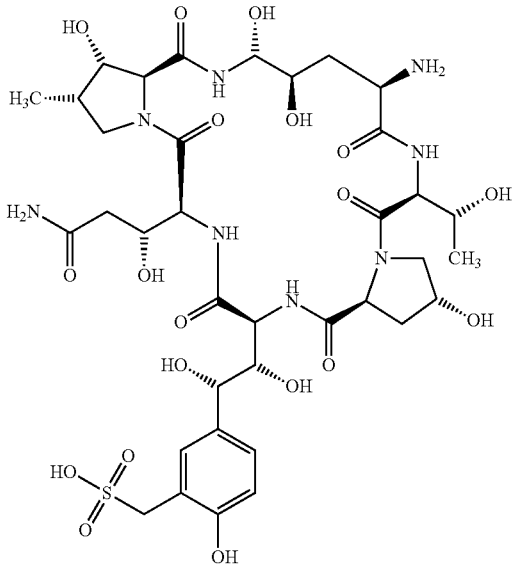

Subsequent acylation introducing alternative side chains has been the subject of several reports. In U.S. Pat. No. 5,965,525 the acylation of a precursor for anidulafungin, a compound herein referred to as echinocandin B nucleus ($C_{34}H_{51}N_7O_{15}$; formula (C); (2R,6S,9R,11R,12R,14aS,15S,16S,20S,23S,25aS)-9-amino-23-((1S,2S)-1,2-dihydroxy-2-(4-hydroxyphenyethyl)-2,11,12,15-tetrahydroxy-6,20-bis ((R)-1-hydroxyethyl)-16-methylhexadecahydro-1H-dipyrrolo[2,1-c:2',1'-l][1,4,7,10,13,16]hexaazacyclohenicosine-5,8,14,19,22,25(9H,25aH)-hexaone), has been described using the 2,4,5- trichlorophenol ester of 4"-(pentyloxy)-[1,1':4',1"-terphenyl]-4-carboxylic acid to yield anidulafungin.

Similarly, in U.S. Pat. Nos. 6,107,458 and 6,265,536 the acylation of a precursor for micafungin, compound FR 179642 (CAS 168110-44-9; $C_{35}H_{52}N_8O_{20}S$; formula (D); 5-((1S,2S)-2-((2R,6S,9R,11R,12R,14aS,15S,16S,20S,23S,25aS)-9-amino-20-((R)-3-amino-1-hydroxy-3-oxopropyl)-2,11,12,15-tetrahydroxy-6-((R)-1-hydroxyethyl)-16-methyl-5,8,14,19,22,25-hexaoxotetracosahydro-1H-dipyrrolo[2,1-c:2',1'-l][1,4,7,10,13,16]-hexaazacyclohenicosin-23-yl)-1,2-dihydroxyethyl)-2-hydroxyphenyl hydrogen sulfate), has been described using benzotriazole activation of 4-(5-(4-(pentyloxy)phenyl)isoxazol-3-yl)benzoic acid to yield micafungin.

An improved production of micafungin is described in U.S. Pat. No. 7,199,248. This method also comprises a step of adding the isolated activated micafungin side chain, i.e. 1-[4-[5-(4-pentyloxy)phenyl)isoxazol-3-yl]benzoyloxy]-1H-1,2,3-benzotriazole to the deacylated micafungin peptide core. Ohigashi et al. (Organic Process Research & Development 9, 179 (2005)) discloses an optimized industrial micafungin production process which also involves isolating the activated micafungin side chain. In WO 2012/136498 an approach is presented involving activation of the micafungin side chain in the presence of a carbodiimide coupling reagent and subsequent coupling to the micafungin peptide core in a one-pot procedure.

The approaches for acylation of a cyclic peptide bearing an amino group described above have the disadvantage that hazardous chemicals are used. Although carbodiimides are dehydration agents that are frequently used in peptide chemistry, they have a drawback that many (i.e. dicyclohexylcarbodiimide) are potent allergens. Several clinical reports of individuals who cannot enter rooms where peptide coupling agents are used have been released. It is therefore desirable to avoid the use of carbodiimide-based coupling agents in micafungin production. Benzotriazole derived activating agents on the other hand are in general explosive and for that reason not suitable for industrial or even laboratory use, unless elaborate and expensive safety equipment and procedures are installed.

Hence, there is a need for improved methods for acylating cyclic peptides bearing an amino group that avoid the drawbacks of hazardous auxiliary chemicals.

DETAILED DESCRIPTION OF THE INVENTION

In the context of the present invention, the term "cyclic peptide bearing an amino group" refers to a cyclic peptide that has at least one group —$NH_2$, also referred to as a free amine group.

In a first aspect, the present invention provides a method for acylating a cyclic peptide bearing an amino group comprising the steps of:

(a) Reacting an acid $R_1CO_2H$ with a compound of general formula (1)

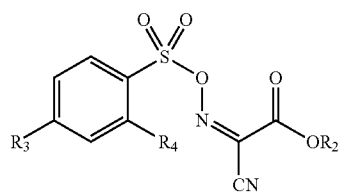

(1)

to give a compound of general formula (2)

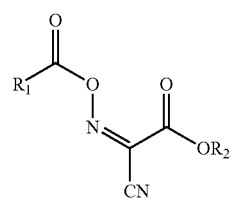

(2)

(b) Mixing said compound of general formula (2) with said cyclic peptide bearing an amino group to form a cyclic lipopeptide, wherein the group $R_1$ is alkyl comprising from 10-25 carbon atoms, preferably from 14-23 carbon atoms, substituted alkyl comprising from 10-25 carbon atoms, preferably from 14-23 carbon atoms, aryl comprising from 10-25 carbon atoms, preferably from 14-23 carbon atoms or substituted aryl comprising from 10-25 carbon atoms, preferably from 14-23 carbon atoms. Preferably $R_1$ is a group that is present in the cyclic peptide obtained according to the method of the invention. Thus, preferred compounds $R_1CO_2H$ are long chain fatty acids such as 10,12-dimethyltetradecanoic acid and substituted benzoic acids such as 4-(octyloxy)benzoic acid, 4-(5-(4-(pentyloxy)phenyl)isoxazol-3-yl)benzoic acid and 4"-(pentyloxy)-[1,1':4',1"-terphenyl]-4-carboxylic acid. Most preferably, $R_1CO_2H$ is 4"-(pentyloxy)[1,1':4',1"-terphenyl]-4-carboxylic acid or 4-(5-(4-(pentyloxy)phenyl)isoxazol-3-yl)benzoic acid, the first being the amide side chain as present in anidulafungin, the second one being the amide side chain as present in micafungin.

The group $R_2$ is a carboxylic acid protecting group such as an alkyl or substituted alkyl, an aryl or substituted aryl. Preferably $R_2$ is a short chain alkyl group such as iso-butyl, n-butyl, sec-butyl, tert-butyl, ethyl, methyl, iso-propyl or n-propyl, more preferably $R_2$ is ethyl. The groups $R_3$ and $R_4$ may be both hydrogen, however preferably either $R_3$ or $R_4$ or $R_3$ and $R_4$ or chosen such that they influence the reactivity of the compound of general formula (1). The skilled person is aware how to achieve such in order to obtain a desired reactivity for a particular substrate. $R_3$ and $R_4$ may groups that have an electronic effect such as electron withdrawing groups or electron donating groups or groups that have a steric effect. Preferred substituents $R_3$ and $R_4$ (see also Palakurthy et al., Eur. J. Org. Chem. 2013, 2627-2633) are alkyl groups like ethyl and methyl, substituted alkyl groups like tert-butyl and iso-propyl, halogens like bromine, chlorine, fluorine and iodine and nitro ($NO_2$) groups. In the context of the present invention preferably $R_3$ is hydrogen, methyl or $NO_2$ and $R_4$ is hydrogen, methyl or $NO_2$. Most preferably $R_3$ is hydrogen and $R_4$ is $NO_2$ or $R_3$ is $NO_2$ and $R_4$ is hydrogen.

In one embodiment the cyclic lipopeptide obtained in step (b) is isolated, for example using techniques such as precipitation, crystallization, lyophilization and the like. Hence the method of the first aspect further comprises the step of isolating the cyclic lipopeptide.

The preferred cyclic peptides to be acylated are cyclic peptides that form the core structure of medicinally useful echinocandins anidulafungin, caspofungin, cilofungin and micafungin. Hence, preferred cyclic peptides are the echinocandin B nucleus (de-acylated echinocandin B; (C)), FR 179642 (D), de-acylated pneumocandin $A_0$ and de-acylated pneumocandin $B_0$.

The method of the present invention may be carried out in various solvents depending also on the solubility of the substrates and products. One preferred example is N,N-dimethylformamide. Usually the first step of the reaction leading to the compound of general formula (2) proceeds quickly and can be completed in 1 to 60 min, preferably from 5 to 30 min. Subsequent reaction with a cyclic peptide in general can be completed within 30 minutes to 6 hours. The foregoing time ranges are at ambient temperature, such as 20±5° C. Lower temperatures may also be used to prevent occurrence of degradation of substrates and/or products. Advantageously, the method of the present invention is carried out in the presence of a base. A preferred base is diisopropylamine. Isolating the final product cyclic lipopeptide can be effected according to known procedures such as precipitation or crystallization and the like.

In one embodiment, the intermediate activated carboxylic acid compound of general formula (2) is isolated. Although the chemical structure of these so-called oxyma-esters of substituted benzoic acids has been proposed for 4-(5-(4-(pentyloxy)phenyl)isoxazol-3-yl)benzoic acid in WO 2012/136498, actual isolation is not described in the prior art. Advantageously, an intermediate isolation of the compound of general formula (2) can be employed to introduce additional purification if needed. In addition isolation of the intermediate can be advantageous to solve certain logistic problems.

The general concept of acylation by activating a carboxylic acid with a compound of general formula (1) is known from Dev D. et al. (*J. Org. Chem.* 79, 5420 (2014)). This document discloses the use of ethyl 2-cyano-2-(2-nitrobenzenesulfonyloxyimino)acetate (o-nosylOXY) for the formation of a variety of esters from alcohols and acids and amides from amines and acids. However, this study is silent on the suitability of o-nosylOXY in more complex situations wherein multiple reactive groups are present in one substrate. Since o-nosylOXY-activated acids are shown to be reactive with all tested amines and, importantly also all tested alcohols, it is not expected this approach is suitable to selectively form an amide in a molecule like FR 179642 (or other cyclic peptides bearing an amino group) that comprises a single amino group and 9 hydroxyl groups of various reactivity. Moreover, FR 179642 also comprises a sulfonic acid group, the reactivity of which towards o-nosylOXY-activated acids is not known so that suitability of the application of this technology in acylation of cyclic peptides bearing an amino group is without precedent. At first hand it would be obvious to protect hydroxyl groups and sulfonic acid groups prior to reaction with o-nosylOXY-activated acids. Surprisingly however, according to the present invention complex substrates bearing multiple functional groups that all are prone to acylation can be selectively acylated at a single amino group in high yield without the need for protection of other functionalities.

The method of the present invention conveniently avoids the need to use allergenic carbodiimides or dangerous benzotriazole derivatives. Furthermore, the method of the present invention is versatile as it is applicable in a one-pot procedure but also using an intermediate purified activated side chain.

In a second aspect, the present invention provides a compound of general formula (2) wherein $R_1$ is 9,11-dimethyltridecyl, 4-(octyloxy)phenyl or 4-(5-(4-(pentyloxy)phenyl)isoxazol-3-yl)phenyl and wherein $R_2$ is ethyl or methyl. In a preferred embodiment, the present invention provides a compound of general formula (2) wherein $R_1$ is 4-(5-(4-(pentyloxy)phenyl)isoxazol-3-yl)phenyl and $R_2$ is ethyl or methyl.

In a third aspect, the present invention provides the use of compounds of general formula (2) in the preparation of anidulafungin and micafungin. In one embodiment, the present invention provides the use of a compound of general formula (2) wherein $R_1$ is 4-(pentyloxy)-1,1':4',1''-terphen-4''-yl and $R_2$ is ethyl or methyl in the preparation of anidulafungin. With the 4-(pentyloxy)-1,1':4',1''-terphen-4''-yl being typical for anidulafungin, the compound of general formula (2) wherein $R_1$ is 4-(pentyloxy)-1,1':4',1''-terphen-4''-yl can be used in approaches alternative to the method of the first aspect. In another embodiment, the present invention provides the use of a compound of general formula (2) wherein $R_1$ is 4-(5-(4-(pentyloxy)phenyl)isoxazol-3-yl)phenyl and $R_2$ is ethyl or methyl in the preparation of micafungin. With the 4-(5-(4-(pentyloxy)phenyl)isoxazol-3-yl)phenyl being typical for micafungin, the compound of general formula (2) wherein $R_1$ is 4-(5-(4-(pentyloxy)phenyl)isoxazol-3-yl)phenyl can be used in approaches alternative to the method of the first aspect. For example FR 179642-like structures wherein certain functionalities other than the amine group are protected may also be acylated with the compound of general formula (2) wherein $R_1$ is 4-(5-(4-(pentyloxy)phenyl)isoxazol-3-yl)phenyl.

Accordingly, in a first embodiment the present invention provides a method for the preparation of anidulafungin or a pharmaceutically acceptable salt thereof comprising the steps of:

(a) Contacting echinocandin B nucleus ($C_{34}H_{51}N_7O_{15}$; formula (C);
(2R,6S,9R,11R,12R,14aS,15S,16S,20S,23S,25aS)-9-amino-23-((1S,2S)-1,2-dihydroxy-2-(4-hydroxyphenyl)ethyl)-2,11,12,15-tetrahydroxy-6,20-bis((R)-1-hydroxyethyl)-16-methylhexadecahydro-1H-dipyrrolo[2,1-c:2',1'-l][1,4,7,10,13,16]-hexaazacyclohenicosine-5,8,14,19,22,25(9H,25aH)-hexaone) with a compound of general formula (2)

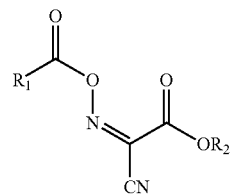

(2)

wherein $R_1$ is

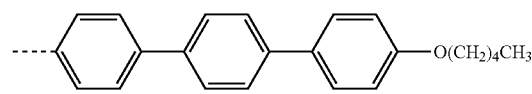

and $R_2$ is ethyl or methyl in the presence of a base;
(b) Isolating the anidulafungin salt obtained in step (a);
(c) Converting the anidulafungin salt obtained in step (b) into a pharmaceutically acceptable salt of anidulafungin;
(d) Isolating said pharmaceutically acceptable salt of anidulafungin obtained in step (c).

In a second embodiment the present invention provides a method for the preparation of micafungin or a pharmaceutically acceptable salt thereof comprising the steps of:

(a) Contacting FR 179642 with a compound of general formula (2)

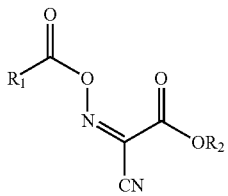

wherein $R_1$ is

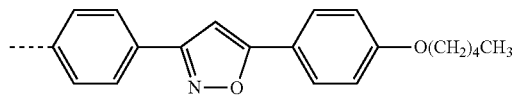

and $R_2$ is ethyl or methyl in the presence of a base;
(b) Isolating the micafungin salt obtained in step (a);
(c) Converting the micafungin salt obtained in step (b) into a pharmaceutically acceptable salt of micafungin;
(d) Isolating said pharmaceutically acceptable salt of micafungin obtained in step (c).

Preferably said base in the above embodiments is an amine, preferred examples of which are tri-alkyl amines such as triethylamine and diisopropylethylamine.

The method of the third aspect results in compositions of anidulafungin or micafungin or pharmaceutically acceptable salts thereof which are of high purity and contain only very low traces of the acylating agents of the present invention or remnants thereof. Thus, the present invention provides a composition comprising:
(a) Anidulafungin or micafungin;
(b) A compound of general formula (2)

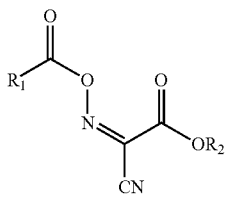

In the above, $R_1$ is

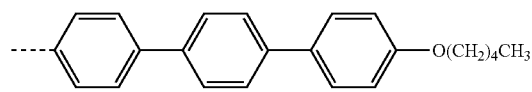

in case of anidulafungin and $R_1$

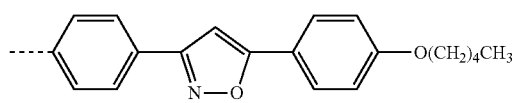

is in case of micafungin.

In both cases, $R_1$ can also be OH. Substituent $R_2$ can be ethyl or methyl and the amount of said compound of general formula (2) relative to the total weight of said composition is from 0.01% w/w to 0.3% w/w, preferably of from 0.015% w/w to 0.2% w/w, most preferably of from 0.01% w/w to 0.15% w/w, still most preferably of from 0.005% w/w to 0.1% w/w.

The invention is hereby illustrated with the following non-limiting examples.

EXAMPLES

Determination of accurate m/z values was performed via direct infusion using the Fusion orbitrap. A 1 mg/mL solution (see Examples for solvent used) was analyzed using continuous infusing whereby no LC is used but the solution directly is introduced into the mass spectrometer. For better ionization the sample was mixed with a solution containing water/acetonitrile/formic acid 50/50/0.1% v/v/v. Mixing ratio was 1:9 sample:added solution. The HRMS (High Resolution Mass Spectrometry) used was a Fusion orbitrap (Thermo Electron) equipped with an electrospray ionization source operated in the positive-ion mode, scanning from m/z 50-800 using a resolution of 15000.

HPLC analysis was carried out using the following method:
Column: GL science ODS-3 150*4.6 mm 5 μm
Column temp: 30° C.
Inj. volume: 5 or 10 μl
Flow rate: 1.0 mL/min
Wavelength: 210 and 275 nm
Mobile phase A: 0.5% $NaH_2PO_4.H_2O$
Mobile phase B: 100% acetonitrile
Gradient:

| Time (min) | A % | B % |
|---|---|---|
| 0 | 97 | 3 |
| 3 | 97 | 3 |
| 10 | 25 | 75 |
| 20 | 25 | 75 |
| 21.0 | 10 | 90 |
| 30 | 10 | 90 |
| 32 | 97 | 3 |
| 37 | 97 | 3 |

Oxyma ester of 4-(5-(4-(pentyloxy)phenyl)isoxazol-3-yl) benzoic acid: RT 24.7 min.
Ethyl 2-cyano-2-(4-nitrobenzenesulfonyloxyimino)acetate: RT 12.7 min.
p-Nitrobenzenesulfonylchloride: RT 12.4 min.
Ethyl 2-cyano-2-(2-nitrobenzenesulfonyloxyimino)acetate: RT 12.2 min.
o-Nitrobenzenesulfonylchloride: RT 12.0 min.
Micafungin: RT 10.9 min.
(Hydroxyimino)cyanoacetate: RT 9.4 min.
FR-179642: RT 5.2 min.

Ethyl 2-cyano-2-(2-nitrobenzenesulfonyloxyimino) acetate ($C_{11}H_9N_3O_7S$, MW 327.27)

Under nitrogen diisopropylamine (DIPEA; 2.175 mL, 12.5 mmol) was added to a stirred solution of ethyl (hydroxyimino)cyanoacetate (Oxyma; 1775 mg; 12.5 mmol) in 5 mL of dichloromethane at 0-10° C. The reaction mixture was cooled to 0° C. followed by addition of 2-nitrobenzenesulfonyl chloride (2770 mg; 12.5 mmol) and stirring was continued for 90 minutes at about 20° C. The reaction mixture was diluted with 25 mL dichloromethane and was washed with 5% hydrochloric acid (3×12.5 mL). The organic phase was dried with anhydrous $CaCl_2$, filtered and concentrated under vacuum at 30° C. to 11 g. Under stirring 10 mL n-heptane was added drop-wise in 90 minutes between 25 and 30° C. The mixture was cooled to 0-5° C. and filtered. The crystals were successively washed with a mixture of dichloromethane/n-heptane=1/1 (v/v) of 0-5° C., and dried under vacuum at 20° C. Yield 3.54 g off-white crystals (86%). Structure confirmation was performed using $^1$H NMR and $^{13}$C NMR. Sample purity was determined using quantitative $^1$H NMR with internal standard dimethyl sulfone in pyridine-$d_5$, recorded on a Bruker 600 MHz Avance spectrometer, equipped with a cryo probe, with standard quantitative parameters, D1=30 s and sample temperature of 300K to be 98.8%. $^1$H NMR (600 MHz, pyridine-d5) δ ppm: 8.4 (d, J=7.8 Hz, 1H), 8.1 (d, J=7.8 Hz, 1H), 7.9 (t, J=7.8 Hz, 1H), 7.7 (t, J=7.8 Hz, 1H), 4.3 (q, J=7.3 Hz, 2H), 1.05 (t, J=7.1 Hz, 3H). $^{13}$C NMR (150 MHz, DMSO-d6) δ ppm: 13.8, 63.7, 106.9, 125.0, 125.8, 132.5, 133.7, 135.0, 137.8, 147.8, 155.4. m/z (in acetonitrile): 328.02366 (theoretical value=328.02340).

Ethyl 2-cyano-2-(4-nitrobenzenesulfonyloxyimino) acetate ($C_{11}H_9N_3O_7S$, MW 327.27)

Under nitrogen diisopropylamine (DIPEA; 2.175 ml, 12.5 mmol) was added to a stirred solution of ethyl (hydroxyimino)cyanoacetate (Oxyma; 1775 mg; 12.5 mmol) in 5 mL of dichloromethane at 0-10° C. The reaction mixture was cooled to 0° C. followed by addition of 4-nitrobenzenesulfonyl chloride (2770 mg; 12.5 mmol) and stirring was continued for 120 minutes at about 20° C. The reaction mixture was diluted with 25 mL dichloromethane and was washed with 5% hydrochloric acid (3×12.5 mL). The organic phase was dried with anhydrous $CaCl_2$, filtered and concentrated under vacuum at 30° C. to 13 g. Under stirring 13 ml n-heptane was added drop-wise in 90 minutes between 25 and 30° C. The mixture was cooled to 0-5° C. and filtered. The crystals were successively washed with a mixture of dichloromethane/n-heptane=1/1 (v/v) of 0-5° C., and dried under vacuum at 20° C. Yield 3.39 g off-white crystals (83%). HPLC: 93 area % of the title compound.

Example 1

One-Pot Conversion of FR 179642 into the Diisopropylamine Salt of Micafungin Using Ethyl 2-cyano-2-(2-nitrobenzenesulfonyloxyimino)acetate Under nitrogen diisopropylamine (0.56 mL; 3.2 mmol) was added to a stirred mixture of ethyl 2-cyano-2-(2-nitrobenzenesulfonyloxyimino)acetate (328 mg; 1 mmol) and 4-(5-(4-(pentyloxy)phenyl)isoxazol-3-yl)benzoic acid (352 mg; 1 mmol) in N,N-dimethylformamide (5 mL). The reaction mixture was stirred for 5 min. Next, FR 179642 ((D); CAS 168110-44-9; 936 mg; 1 mmol) was added and the mixture was stirred for 5.5 hours at about 20° C. The reaction mixture was diluted with ethyl acetate (30 mL) and stirred at about 20° C. for 1 hour. The precipitate was successively filtered off, washed with acetone (25 mL), washed with ethyl acetate (25 mL) and dried under vacuum at about 20° C., yielding 1176 mg of the diisopropylamine salt of micafungin as an off-white powder (84% yield). HPLC (area %): 88% diisopropylamine salt of micafungin (RT 10.9 min.). $^1$H NMR (600 MHz, methanol-d4) δ ppm: 1.0 (t, J=7.3 Hz, 3H), 1.1 (d, J=6.8 Hz, 3H), 1.2 (m, 3H), 1.4 (m, 15H), 1.4 (m, 2H), 1.5 (m, 2H), 1.8 (m, 2H), 2.0 (m, 2H), 2.2 (m, 2H), 2.4 (dd, J=13.7 & 7.9 Hz, 1H), 2.5-2.6 (m, 2H), 2.9 (m, 1H), 3.2 (q, J=7.4 Hz, 2H), 3.4 (t, J=9.7 Hz, 1H), 3.8 (d, J=11.1 Hz, 1H), 3.9 (dd, J=11.3 & 2.8 Hz, 1H), 4.1 (t, J=6.5 Hz, 2H), 4.1 (m, 3H), 4.2 (s, 1H), 4.3 (m, 1H), 4.4-4.5 (m, 4H), 4.5-4.6 (m, 3H), 4.7 (dd, J=11.3 & 5.6 Hz, 1H), 5.0 (d, J=2.8 Hz, 1H), 5.1 (m, 1H), 5.3 (d, J=2.03 Hz, 1H), 6.9 (d, J=8.3 Hz, 1H), 7.05 (m, 3H), 7.1 (s, 1H), 7.3 (d, J=1.7 Hz, 1H), 7.8 (d, J=8.5 Hz, 2H), 8.0 (s, 4H).

Example 2

One-Pot Conversion of FR 179642 into the Diisopropylamine Salt of Micafungin Using Ethyl 2-cyano-2-(4-nitrobenzenesulfonyloxyimino)acetate Under nitrogen diisopropylamine (0.56 mL; 3.2 mmol) was added to a stirred mixture of ethyl 2-cyano-2-(4-nitrobenzenesulfonyloxyimino)acetate (328 mg; 1 mmol) and 4-(5-(4-(pentyloxy)phenyl)isoxazol-3-yl)benzoic acid (352 mg; 1 mmol) in N,N-dimethylformamide (5 mL). The reaction mixture was stirred for 5 min. Next FR 179642 ((D); CAS 168110-44-9; 936 mg; 1 mmol) was added and the mixture was stirred for 2 hours at about 20° C. The reaction mixture was diluted with N,N-dimethylformamide (1 mL) and ethyl acetate (30 mL) was added under stirring. Stirring was continued at about 20° C. for 1 hour. The precipitate was successively filtered off, washed with acetone (30 mL), washed with ethyl acetate (25 mL), and dried under vacuum at about 20° C., yielding 1146 mg of the diisopropylamine salt of micafungin as an off-white powder (82% yield). HPLC (area %): 90% diisopropylamine salt of micafungin (RT 10.9 min).

Comparative Example

Oxyma Ester of 4-(5-(4-(pentyloxy)phenyl)isoxazol-3-Yl)benzoic acid Using EDC

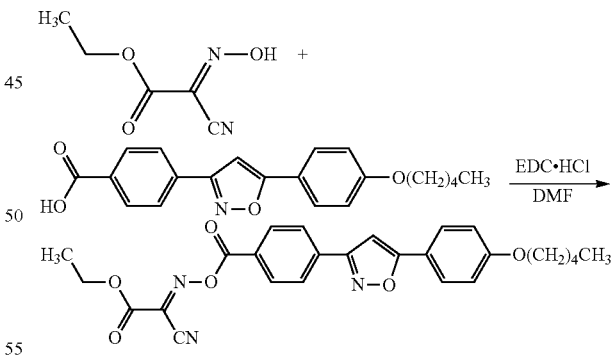

Under nitrogen 4-(5-(4-(pentyloxy)phenyl)isoxazol-3-yl) benzoic acid (FR-195752; 6.0 g, 17.1 mmol) and ethyl (hydroxyimino)cyanoacetate (Oxyma; 97%; 2.75 g; 18.8 mmol) were suspended in DMF (150 mL) at about 20° C. N-(3-Dimethylaminopropyl)-N'-ethylcarbodiimide hydrochloride (EDC.HCl, 3.60 g, 18.8 mmol) was added, and the mixture was stirred at about 20° C. for 4.5 h. A conversion of >97% was obtained as measured by H PLC. The mixture was diluted with water (750 mL) and ethyl acetate (900 mL). The phases were separated and the aqueous phase was back-extracted once with ethyl acetate (450 mL). The organic phases were combined and successively washed with water and dried on magnesium sulfate, filtered and concentrated under vacuum at 30° C. until concentrate (200 mL). Crystals were allowed to form after which concentration under vacuum was resumed until a volume of 100 mL. The concentrate was cooled to 0-5° C., stirred for one hour after which the crystals were filtered off, washed with cold ethyl acetate and dried under vacuum at 20° C. during 4 hours, yielding 7.35 g of the title compound as yellow crystals. Yield 90.5%. HPLC (area %): 99% (RT 24.7) and 0.3% side chain as free acid. $^1$H NMR (400 MHz, acetone-d6) δ ppm: 8.3 (d, J=8.6 Hz, 2H), 8.2 (d, J=8.6 Hz, 2H), 7.9 (d, J=9 Hz, 2H), 7.4 (s, J=Hz, 1H), 7.1 (d, J=9 Hz, 2H), 4.5 (q, J=7.2 Hz, 2H), 4.1 (t, J=6.5 Hz, 2H), 1.8 (m, 2H), 1.5 (m, 2H), 1.4 (m, 2H), 1.4 (t, J=7 Hz, 3H), 0.9 (t, J=7.3 Hz, 3H). $^{13}$C NMR (100 MHz, acetone-d6) δ ppm: 14.3, 14.4, 23.2, 28.7, 29.4, 64.7, 68.8, 97.6, 108.1, 108.5, 116.0, 120.5, 128.3, 128.3, 131.8, 133.9, 136.4, 158.0, 161.1, 162.0, 162.6, 172.0. m/z (in acetone): 476.1813 (theoretical value=476.1816).

Example 3

Oxyma Ester of 4-(5-(4-(pentyloxy)phenyl)isoxazol-3-Yl)benzoic acid Using Ethyl 2-cyano-2-(2-nitrobenzenesulfonyloxyimino)acetate

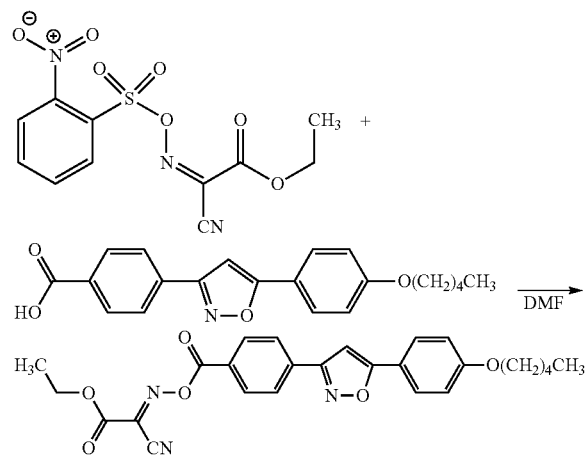

Under nitrogen diisopropylamine (0.19 mL; 1.1 mmol) was added to a stirred mixture of ethyl 2-cyano-2-(2-nitrobenzenesulfonyloxyimino)acetate (213 mg; 0.65 mmol) and 4-(5-(4-(pentyloxy)phenyl)isoxazol-3-yl)benzoic acid (FR-195752; 176 mg; 0.50 mmol) in N,N-dimethylformamide (3.5 mL) and stirring was continued for 10 minutes at 20° C. The reaction mixture was diluted with ethyl acetate (40 mL) and this solution was washed with a saturated sodium bicarbonate solution, washed with 1 M NaCl, and evaporated under vacuum at 30° C. until a volume of approximately 5 mL. Crystals started to form spontaneously. The suspension was cooled to 0-5° C. The crystals were filtered off, washed with cold ethyl acetate, and dried under vacuum at 20° C., yielding 150 mg of the diisopropylamine salt of micafungin as yellow crystals. Yield 63%. HPLC (area %): 98% (RT 24.7).

Example 4

Conversion of FR 179642 into the Diisopropylamine Salt of Micafungin Using Ethyl 2-cyano-2-(2-nitrobenzenesulfonyloxyimino)acetate (1 g Scale)

FR 179642 ((D); CAS 168110-44-9; NMR assay 75%; 1.0 g; 0.80 mmol) was dissolved in 13 mL DMF and cooled to −3° C. Diisopropylethylamine (0.22 g, 0.30 mL, 1.7 mmol) was added at −3° C. followed by addition at −3 to 0° C. of the oxyma ester of 4-(5-(4-(pentyloxy)phenyl)isoxazol-3-yl)benzoic acid (545 mg, 1.15 mmol). The reaction mixture was stirred at 0 to 5° C. for 4.5 hours. The conversion was complete according to HPLC. Under stirring ethyl acetate (65 mL) was added in about 5 minutes to the solution and stirring was continued for about 1 hour. The precipitate was successively filtered off, washed with acetone, washed with ethyl acetate and dried under vacuum for 2 hours at about 20° C., yielding 1.21 g of the title compound as a white powder (NMR assay 92%; 99% yield).

Example 5

Conversion of FR 179642 into the Diisopropylamine Salt of Micafungin Using Ethyl 2-cyano-2-(2-nitrobenzenesulfonyloxyimino)acetate (10 g Scale)

FR-179642 ((D); CAS 168110-44-9; NMR assay 75%; 10.0 g; 10.7 mmol) was dissolved in 130 mL DMF and cooled to −5° C. Diisopropylethylamine (2.2 g, 3.0 mL, 17 mmol) was added at −5° C. followed by addition at −5° C. of the oxyma ester of 4-(5-(4-(pentyloxy)phenyl)isoxazol-3-yl)benzoic acid (5.45 g, 11.5 mmol). The clear reaction mixture was stirred at −5 to 0° C. for 1 hour. The conversion was complete according to HPLC. Under stirring ethyl acetate (650 mL) was added in about 10 minutes to the solution and stirring was continued for about 1 hour. The precipitate was successively filtered off, washed with acetone, washed with ethyl acetate and dried under vacuum for 2 hours at about 20° C., yielding 12.95 g of the diisopropylamine salt of micafungin as a white powder (NMR assay 92.1%). According to HPLC 0.1% FR-179642, 0.1% FR-195752, 3.3% DMF; no activated side-chain and no oxyma.

The invention claimed is:
1. A method for selectively acylating a cyclic peptide bearing an amino group at the amino group without protecting the hydroxyl groups of the cyclic peptide prior to the acylation step, the method comprising the steps of:
(a) reacting an acid $R_1CO_2H$ with a compound of general formula (1)

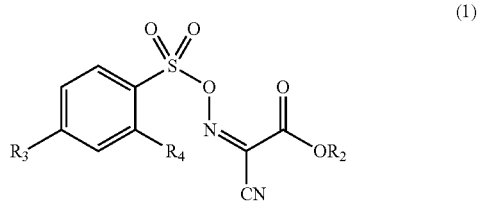

(1)

to give a compound of general formula (2)

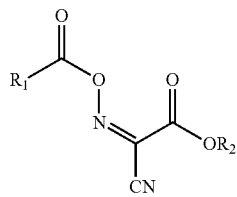
(2)

(b) mixing said compound of general formula (2) with said unprotected cyclic peptide bearing an amino group to selectively acylate the cyclic peptide at the amino group to form a cyclic lipopeptide;
wherein $R_1$ is alkyl comprising from 10-25 carbon atoms, substituted alkyl comprising from 10-25 carbon atoms, aryl comprising from 10-25 carbon atoms or substituted aryl comprising from 10-25 carbon atoms, $R_2$ is alkyl, $R_3$ is alkyl, substituted alkyl, halogen, hydrogen or $NO_2$ and $R_4$ is alkyl, substituted alkyl, halogen, hydrogen or $NO_2$.

2. The method according to claim 1 wherein said cyclic lipopeptide obtained in step (b) is isolated.

3. The method according to claim 1 wherein $R_3$ is hydrogen, methyl or $NO_2$ and $R_4$ is hydrogen, methyl or $NO_2$.

4. The method according to claim 1 wherein $R_1$ is $(CH_2)_8 CH(CH_3)CH_2CH(CH_3)CH_2CH_3$ or

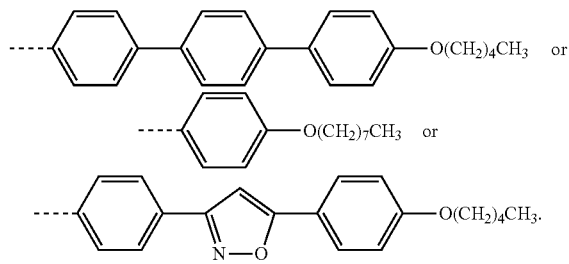

5. The method according to claim 1 wherein said unprotected cyclic peptide bearing an amino group is the echinocandin B nucleus or FR 179642 or salts thereof.

6. The method according to claim 1 wherein said compound of general formula (2) is isolated prior to step (b).

7. A method for the preparation of anidulafungin or a pharmaceutically acceptable salt thereof comprising the steps of:
(a) contacting an unprotected echinocandin B nucleus that is unprotected at the hydroxyl groups with a compound of general formula (2)

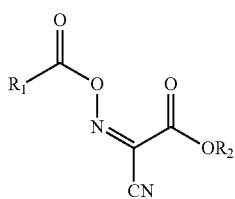
(2)

wherein $R_1$ is

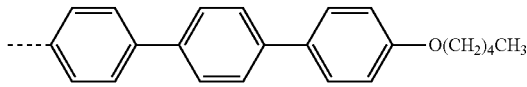

and $R_2$ is ethyl or methyl in the presence of a base to selectively acylate the amino group of the unprotected echinocandin B nucleus;
(b) isolating the anidulafungin salt obtained in step (a);
(c) converting the anidulafungin salt obtained in step (b) into a pharmaceutically acceptable salt of anidulafungin;
(d) isolating said pharmaceutically acceptable salt of anidulafungin obtained in step (c).

8. The method according to claim 7 wherein said base is diisopropylethylamine and said anidulafungin salt is the diisopropylethylamine salt of anidulafungin.

9. The method according to claim 5 wherein said unprotected cyclic peptide bearing an amino group is FR 179642 or a salt thereof.

10. The method according to claim 5 wherein said unprotected cyclic peptide bearing an amino group is the echinocandin B nucleus or a salt thereof.

* * * * *